United States Patent
Dehottay et al.

(10) Patent No.: US 9,475,848 B2
(45) Date of Patent: Oct. 25, 2016

(54) FERMENTATION PROCESS FOR PRODUCING A VIRULENCE FACTOR FROM BORDETELLA

(71) Applicant: GlaxoSmithKline Biologicals S.A., Rixensart (BE)

(72) Inventors: Philippe Marc Helene Dehottay, Rixensart (BE); Philippe Goffin, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/376,274

(22) PCT Filed: Jan. 30, 2013

(86) PCT No.: PCT/EP2013/051743
§ 371 (c)(1),
(2) Date: Aug. 1, 2014

(87) PCT Pub. No.: WO2013/113729
PCT Pub. Date: Aug. 8, 2013

(65) Prior Publication Data
US 2015/0010948 A1    Jan. 8, 2015

Related U.S. Application Data

(60) Provisional application No. 61/593,541, filed on Feb. 1, 2012.

(51) Int. Cl.
C12N 1/38    (2006.01)
C07K 14/235  (2006.01)
C12N 1/20    (2006.01)

(52) U.S. Cl.
CPC .......... *C07K 14/235* (2013.01); *C12N 1/20* (2013.01); *C12N 1/38* (2013.01)

(58) Field of Classification Search
CPC ........................................... C12N 1/38
See application file for complete search history.

(56) References Cited

U.S. PATENT DOCUMENTS 5,985,286 A * 11/1999 Gueirard et al. .......... 424/240.1

FOREIGN PATENT DOCUMENTS

| EP | 0 659 879 | 10/1984 |
| EP | 0 121 249 | 6/1995 |

OTHER PUBLICATIONS

Masure, "Modulation of adenylate cyclase toxin production as Bordatella pertussis enters human macrophages," Proc Natl Acad Sci USA 89:6521-6525, 1992.*
Brickman et al., "Involvement of the BvgAs signal transduction system in production and responsiveness to putative Bordatella intercellular signaling substances," Abstracts of the General Meetings of the American Society for Microbiology, 101:127, 2001.*

(Continued)

*Primary Examiner* — Rosanne Kosson
(74) *Attorney, Agent, or Firm* — Virginia G. Campen (57) ABSTRACT

A process for fermenting *Bordetella* species comprising incubating a sample of bacteria of a *Bordetella* species in a first environment under at least one bvg (*Bordetella* virulence genes) modulating condition, for at least 5 generations, to produce a mature culture, and then incubating the mature culture in a second environment in the absence of the at least one bvg modulating condition.

45 Claims, 3 Drawing Sheets

(56) References Cited

OTHER PUBLICATIONS

Gupta, et al., The effects of different inactivating agents on the potency, toxicity and stability of pertussis vaccine, J. Biol. Standardization, 15:87-98 (1987).

Vaccines, Fifth Edition, (Plotkin et al., Eds.), 2008, Saunders Elsevier, p. 78.

WHO Expert Committee on Biological Standardization, Thirtieth Report (World Health Organization Technical Report Series 638, World Health Organization Geneva (1979)), pp. 1-5, 60-75.

* cited by examiner

FERMENTATION PROCESS FOR PRODUCING A VIRULENCE FACTOR FROM BORDETELLA

This application is filed pursuant to 35 U.S.C. §371 as a United States National Phase Application of International Patent Application Serial No. PCT/EP2013/051743 filed Jan. 30, 2013, which claims priority to U.S. Patent Application No. 61/593,541 filed Feb. 1, 2012 and the contents of each of the foregoing applications are hereby incorporated by reference.

BACKGROUND

The bacterium *Bordetella pertussis* is the causative agent for whooping cough, a respiratory disease that can be severe in infants and young children. The clinical course of the disease is characterised by paroxysms of rapid coughs followed by inspiratory effort, often associated with a characteristic 'whooping' sound. In serious cases, oxygen deprivation can lead to brain damage; however the most common complication is secondary pneumonia.

Whooping cough is usually considered to be caused by *B. pertussis*, but occasionally *B. parapertussis* is isolated from patients with typical signs and symptoms of whooping cough. *B. parapertussis* infection is of lower frequency than *B. pertussis* with 5-10% of whooping cough being associated with *B. parapertussis* (Mertsola (1985) Eur J Clin Microbiol 4; 123; Lautrop (1971) Lancet 1(7711) 1195-1198). *B. parapertussis* is associated with mild clinical symptoms which, combined with its serological cross-reactivity with *B. pertussis*, makes *B. parapertussis* difficult to diagnose.

The first generation of vaccines against *B. pertussis* were whole cell vaccines, composed of whole killed bacteria. These were introduced in many countries in the 1950s and 1960s and were successful at reducing the incidence of whooping cough. A problem with whole cell *B. pertussis* vaccines is the high level of reactogenicity associated with them. Acellular vaccines containing purified *B. pertussis* proteins are less reactogenic and have been adopted for the vaccination programmes of many countries. Acellular vaccines typically containing *pertussis* toxin (PT), filamentous haemagglutinin (FHA) and quite often pertactin (PRN), are widely used and provide effective protection from the severity of whooping cough.

BRIEF SUMMARY

Introduction

In a first aspect there is provided a fermentation process comprising the following steps:
a) providing a sample of bacteria of a *Bordetella* species;
b) incubating the sample of bacteria of a *Bordetella* species in a first environment under at least one bvg (*bordetella virulence genes*) modulating condition for at least 5 generations, thereby producing a mature culture;
c) incubating the mature culture in a second environment in the absence of the at least one bvg modulating condition; wherein step c) occurs after step b).

In a second aspect there is provided a fermentation process comprising the following steps:
a) providing a sample of bacteria of a *Bordetella* species in a first culture medium comprising at least one bvg modulator;
b) incubating the sample in the first culture medium comprising the at least one bvg modulator for at least 5 generations, thereby producing a mature culture;
c) incubating the mature culture in a second culture medium in the absence of the at least one bvg modulator; wherein step c) occurs after step b).

In a third aspect there is provided a fermentation process comprising the following steps:
a) providing a sample of bacteria of a *Bordetella* species in a first culture medium;
b) incubating the sample in the first culture medium comprising at least one bvg modulator for at least 5 generations, thereby producing a mature culture;
c) incubating the mature culture in a second culture medium in the absence of the at least one bvg modulator; wherein step c) occurs after step b).

In a fourth aspect there is provided a virulence factor obtainable by the process.

In a fifth aspect there is provided a virulence factor obtained by the process.

In a sixth aspect there is provided an immunogenic composition comprising the virulence factor and a pharmaceutically acceptable excipient.

In a seventh aspect there is provided a vaccine comprising the immunogenic composition.

In an eighth aspect there is provided a use of the immunogenic composition or the vaccine in the prevention or treatment of disease.

In a ninth aspect there is provided a use of the immunogenic composition or the vaccine in the preparation of a medicament for the treatment or prevention of bacterial disease.

In a tenth aspect there is provided a method of preventing or treating disease comprising administering the immunogenic composition or the vaccine to a patient.

DETAILED DESCRIPTION

General

The inventors have surprisingly found that higher yields of *Pertussis* virulence factors can be obtained by growing *Pertussis* species as described herein in the presence of at least one bvg modulating condition, even though bvg modulating conditions are generally considered to inhibit the expression of virulence factors from *Pertussis* species.

*B. pertussis* can display different phenotypes in terms of virulence. These phenotypes are named Bvg+ and Bvg– (Bvg indicates expression or lack thereof of *Bordetella* virulence genes). The Bvg+ phenotype is a virulent phenotype characterised by high expression of virulence factors such as *pertussis* toxin (PT), filamentous haemagglutinin (FHA) and pertactin (PRN), but also other toxins and adhesins. The Bvg– phenotype is an avirulent phenotype, which does not express virulence factors such as PT or other toxins/adhesins.

The transition between phenotypic states is under control of the two-component regulatory system BvgAS, which directly or indirectly detects environmental conditions such as temperature, sulphate, nicotinic acid, and regulates the expression of genes under its control. Under certain conditions, the sensor protein BvgS auto-phosphorylates, and via a phosphorylation cascade, the phosphoryl group is ultimately transferred to the response regulator BvgA. Active BvgA~P (phosphorylated) binds to the promoter region of the virulence factor genes, and modulates their transcription level. Such a regulation system results in the integration of environmental cues at the level of one single central transcriptional regulator, BvgAS. As an output, *B. pertussis* regulates the expression of virulence factors at the transcriptional level in response to the environmental conditions.

Genes under transcriptional control of the BvgAS system form the Bvg regulon.

Compounds which inhibit production of virulence factors from *pertussis* often act by modulating the bvg genetic locus and hence can be named bvg modulators. Similarly conditions which favour the Bvg+ phenotype may be named bvg modulating conditions.

In general *Bordetella* cells are able to mutate between Bvg+ and Bvg– genotypes. In particular during culture *Bordetella* cells can mutate to the Bvg– genotype via spontaneous mutations. Bvg– genotype cells have the Bvg– phenotype, this means that they produce lower amounts of virulence factors (and thus are undesirable in a fermentation process intended to product high levels of virulence factors). The fact that Bvg– genotype cells produce lower levels of virulence factors provides the Bvg-genotype cells with an advantage over those of the Bvg+ genotype, namely that less of their energy is spent in producing virulence factors allowing them to grow faster. For this reason when *Bordetella* cells are cultured the proportion of cells which have the Bvg-genotype tends to increase over time (known as Bvg– takeover). The present inventors have demonstrated that a higher proportion of cells can be maintained in the Bvg+ genotype by the addition of a Bvg modulating condition. These conditions, as explained above, favour the Bvg– phenotypic state and the presence of such a condition allows the *Bordetella* to express the Bvg– phenotype (whilst maintaining their Bvg+ genotype). This removes the competitive advantage of the Bvg– genotype cells meaning that the proportion of Bvg– genotype cells in the final culture is lower. During the growth phase of the fermentation *Bordetella* can be grown under these bvg modulating conditions until a desired mass of Bvg+ genotype cells is reached. Once the mass of *Bordetella* cells is sufficiently high the bvg modulating condition can be removed allowing the Bvg+ genotype cells to return to the Bvg+ phenotype and express high levels of the virulence factors.

For the avoidance of doubt any references to 'Bvg+ cells' or 'bvg+ cells' refers to cells having the Bvg+ genotype, similarly any references to 'Bvg– cells' or 'bvg– cells' refers to cells having the Bvg– genotype.

Thus the present inventors have found that a process for fermenting a *Bordetella* species can be improved by adding a step of growing a *Bordetella* species in at least one bvg modulating condition, this ensures that *Bordetella* can grow to high mass whilst maintaining a high proportion of the *Bordetella* cells in the Bvg+ genotype and when sufficient cell mass is reached the bvg modulating condition can be removed leaving a culture containing a high proportion of Bvg+ genotype cells expressing virulence factors at a high level. This leads to increased yield of virulence factors produced from the *Bordetella* species. This is despite the fact that, in general, bvg modulating conditions as defined herein lead to reduction of expression of virulence factors.

Accordingly in a first embodiment there is provided a fermentation process comprising the following steps:
a) providing a sample of bacteria of a *Bordetella* species;
b) incubating the sample of bacteria of a *Bordetella* species in a first environment under at least one bvg (*bordetella* virulence genes) modulating condition for at least 5 generations, thereby producing a mature culture;
c) incubating the mature culture in a second environment in the absence of the at least one bvg modulating condition;
wherein step c) occurs after step b).

Step b) describes a step in which a bvg modulating condition is present and the *Bordetella* culture is growing in order to provide sufficient cell mass for high expression whilst preserving the Bvg+ genotype (reducing the takeover of Bvg– cells). The *Bordetella* species should then be transferred into conditions in the absence of the bvg modulating condition to allow expression of virulence factors (step c). The *Bordetella* species can be exposed to the bvg modulating condition early in the fermentation process, for example the bvg modulating condition can be used during a step of cell banking. Alternatively the bvg modulating condition can be added at a later stage such as during pre-culture.

The term fermentation process' refers to an industrial-scale (for example 20 liter or more) process for growing cells and/or expressing a protein from those cells. In this case the process of the disclosure may be used for expressing high concentrations of virulence factors from the *Bordetella* species. Alternatively other applications are envisioned, for example the process can be used to grow the *Bordetella* species for use in making whole cell *Bordetella* vaccines. Optionally the fermentation process is a process for production of one or more toxins from the *Bordetella* species. In one embodiment the process is a process for preserving the *Bordetella* species in a bvg+ genotype in industrial culture. In one embodiment the process is a process for preventing loss of expression of virulence factors in growth in industrial culture. In one embodiment the process is a process for enhancing production of virulence factors of the *Bordetella* species.

The term '*Bordetella* species' refers to a species of the *Bordetella* genus including but not limited to *Bordetella pertussis*, *Bordetella parapertussis* and *Bordetella bronchiseptica*, preferably *Bordetella pertussis*.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The terms "comprising", "comprise" and "comprises" herein are intended by the inventors to be optionally substitutable with the terms "consisting of", "consist of", and "consists of", respectively, in every instance.

The abbreviation, "e.g." is derived from the Latin exempli gratia, and is used herein to indicate a non-limiting example. Thus, the abbreviation "e.g." is synonymous with the term "for example."

Step a)

Step a) describes the phase of the fermentation process prior to exposing the *Bordetella* species to the bvg modulating condition; this generally refers to a step of providing a sample of a quantity of live *Bordetella* bacteria. The medium which is inoculated can be a solid or a liquid medium. In one embodiment the process further comprises a step i) of selecting a sample of the bacteria of a *Bordetella* species, wherein the sample of the bacteria is predominantly Bvg+ genotype and wherein step i) takes place before step a). Optionally more than 50%, more than 60%, more than 70%, more than 75%, more than 80%, more than 85%, more than 90%, more than 95%, more than 98%, between 85% and 100%, between 90% and 100%, between 95% and 100% or between 98% and 100% of the sample of the bacteria is Bvg+ genotype in step a).

The process of the disclosure reduces the takeover of Bvg– genotype cells and so it is advantageous to begin the process using a sample of the *Bordetella* species which is predominantly Bvg+ genotype.

The sample used in step a) may be obtained from any source, for example the sample could be selected from a cell line held within a laboratory or may be obtained from an institution such as the ATCC (American Type Culture Collection).

Step b

Step b) describes exposing the sample of step a) to at least one bvg modulating condition, such a condition can be any condition which reduces the takeover of Bvg– genotype cells or preserves the Bvg+ genotype. Without being bound by theory, when *Bordetella* is incubated in culture (for example in a laboratory or a manufacturing facility) the proportion of the cells which are Bvg– genotype tends to increase over time (several generations). This may be due to a selective advantage resulting from not expressing virulence factors which have no benefit to the *Bordetella* in culture. For this reason incubating *Bordetella* in the presence of a condition which reduces expression of virulence factors reduces the selective advantage from converting to Bvg– genotype, thus reducing the takeover of Bvg– genotype cells in culture. Thereby maintaining the Bvg+ genotype population in the sample.

For this reason bvg modulating conditions include conditions which reduce expression of virulence factors. A 'bvg modulating condition' is, optionally, a condition which prevents an increase in the proportion of Bvg– genotype cells by more than 25 times, 15 times, 10 times, 9 times, 8 times, 7 times, 6 times, 5 times, 4, 3 times, 2 times, 1.5 times, after growth in culture for 5, 6, 7, 8, 9, 10, 11, 12, 13, 14, 15 or more generations. A generation refers to the time it takes for the number of bacteria in a culture to double which is approximately 4 hours for *Bordetella pertussis*, however this varies depending on the conditions under which the *Bordetella pertussis* is grown. It is possible to determine whether a potential bvg modulating condition is, in fact, a bvg modulating condition by growing cells under the potential bvg modulating condition for at least 8 generations, and plating the cells on Bordet-Gengou medium (which contains 5% blood) (Bordet J and Gengou O, Le Microbe de la coqueluche, Annales de l'Institut Pasteur 1906; 20:731-41), in order to obtain single colonies. On BG medium, Bvg+ genotype cells appear as domed, compact, haemolytic colonies, whereas Bvg– genotype cells appear as flat, non-haemolytic colonies. The results of this test should be compared to cells which were grown under the same conditions but without the use of the potential bvg modulating condition. If the proportion of Bvg– genotype cells is significantly lower than the proportion of Bvg− genotype cells in the reference sample the condition is a bvg modulating condition.

Any bvg modulating condition can be used in the context of the present disclosure; particular examples include high or low pH conditions, low oxygen conditions, low temperature conditions or the presence of a bvg modulator.

The phrase 'bvg modulator' refers to a compound in a suitable concentration (a modulatory concentration) which reduces the take-over of Bvg− genotype cells. The concentration of the bvg modulator is not necessarily constant throughout step b) but remains within a modulatory concentration throughout step b). For example niacin at various concentrations including 0.604 g/L is a bvg modulator. In general compounds which inhibit expression of toxins, such as *Pertussis* Toxin, from *Bordetella pertussis* are bvg modulators.

Step b) refers to any phase of a fermentation process in which at least one bvg modulating condition is present, for example this step can include cell banking and/or pre-culture and/or large scale fermentation. The term 'cell banking' is clear to a person skilled in the art. In general cell banking involves preparing a strain of bacteria for storage and can involve taking a clone of bacteria (which can be the inoculum referred to above) and incubating the clone of bacteria until a small volume of bacteria is obtained. Samples of this volume of bacteria can be prepared, flash frozen and kept in a freezer. Pre-culture generally involves taking a starter culture and allowing the cells to reproduce in order to reach a sufficient concentration of cells for the next step in the process, for example virulence factor expression. This can involve several small incubations, for example a small sample of *Bordetella* can be grown in a small shake flask, and the contents of this small shake flask may be transferred to a larger shake flask. This can even involve a step in which the cells are grown in a small fermentor.

Optionally a pre-culture phase can comprise production of approximately 8, 9 10, 11, 12, 13, 14, 15, 16, 17, 18 generations of *Pertussis*. Optionally the pre-culture phase is between 1 hour and 200 hours, between 2 hours and 150 hours, between 5 hours and 125 hours, between 10 hours and 100 hours, between 20 hours and 50, greater than or equal to 1 hour, greater than or equal to 2 hours, greater than or equal to 5 hours, greater than or equal to 10 hours, greater than or equal to 20 hours, greater than or equal to 50 hours, less than or equal to 200 hours, less than or equal to 150 hours, less than or equal to 125 hours, less than or equal to 100 hours or less than or equal to 50 hours. Optionally the pre-culture phase is carried out in a vessel less than 10 liters, less than 8 liters, less than 5 liters, between 1 and 10 liters, between 1 and 8 liters, between 1 and 5 liters, between 1 and 3 liters, between 2 and 8 liters, between 2 and 5 liters or between 2 and 3 liters.

During step b) the *Bordetella* is grown in a 'first environment', which refers to an environment which comprises the bvg modulating condition. For example this environment may refer to an oxygen deprived environment or a high pH environment. The term 'environment' can also refer to a medium comprising the at least one bvg modulator. The first environment may therefore refer to a first culture medium comprising at least one bvg modulator and the second environment can refer to a second culture medium not comprising at least one bvg modulator. Optionally the at least one bvg modulating condition comprises presence of at least one bvg modulator in the first culture medium. Optionally the first and second culture medium are the same. Optionally the first and second culture medium are different. Optionally the second culture medium comprises Stainer Scholte medium. Alternatively the second culture medium comprises modified Stainer Scholte medium. The composition of Stainer Scholte medium is described in Cohen and Wheeler, *American Journal of Public Health* (1946) 36: 371-376. A medium is a modified Stainer Scholte medium if it contains essentially the same medium components at essentially the same concentrations, however, containing modification of the concentration of between 1 and 5 of the medium components, lacking between 1 and 3 of the medium components, or containing between 1 and 20 additional medium components.

Step b) results in the production of a mature culture which can be used for step c), The phrase 'mature culture' refers to an inoculum which has been grown in the presence of at least one bvg modulating condition for at least 5 generations.

Optionally at least part of step b) is carried out in a vessel between 50 ml and 25 liters, between 50 ml and 20 liters, between 50 ml and 15 liters between 50 ml and 10 liters, between 50 ml and 5 liters, less than or equal to 25 liters, less than or equal to 20 liters, less than or equal to 15 liters, less than or equal to 10 liters, less than or equal to 5 liters, greater than or equal to 25 ml, greater than or equal to 50 ml, greater than or equal to 100 ml, greater than or equal to 250 ml, greater than or equal to 500 ml, greater than or equal to 1 liter or greater than or equal to 2 liters in volume.

Optionally step c) is carried out in a fermentor. The fermentor working volume can be between 5 and 10000 liters, between 10 and 5000 liters, between 20 and 2000 liters 50 liters and 1000 liters, greater than or equal to 5 liters, greater than or equal to 10 liters, greater than or equal to 15 liters, greater than or equal to 20 liters, greater than or equal to 25 liters, greater than or equal to 50 liters, greater than or equal to 100 liters, less than or equal to 10000 liters, less than or equal to 5000 liters or less than or equal to 2500 liters.

Optionally step b) comprises a cell banking phase. Alternatively cell banking occurs between step a) and step b).

In one embodiment step b) comprises at least 5, 6, 7, 8, 9, 10, 12, 14, 16, or 17 generations. Optionally step b) comprises less than 40, less than 35, less than 30, less than 25, less than 20 or less than 18 generations. Optionally step b) is less than or equal to 200 hours, less than or equal to 150 hours, less than or equal to 100 hours, less than or equal to 80 hours, less than or equal to 70 hours, less than or equal to 60 hours, less than or equal to 55 hours, more than or equal to 10 hours, more than or equal to 15 hours, more than or equal to 20 hours, more than or equal to 25 hours, more than or equal to 30 hours, more than or equal to 35 hours, more than or equal to 40 hours, between 10 hours and 200 hours, between 15 hours and 150 hours, between 20 hours and 100 hours, between 25 hours and 80 hours or between 30 hours and 70 hours.

In an embodiment step b) is carried out at a temperature of between 20° C. and 45° C., between 22° C. and 43° C., between 24° C. and 42° C., between 28° C. and 42° C., between 30° C. and 42° C., or between 32° C. and 40° C.

In an embodiment step b) is carried out at a pH of between 6.5 and 7.8, between 6.7 and 7.5, between 6.9 and 7.3 or between 7.0 and 7.2.

In an embodiment step b) is carried out in the presence of between 10% and 50%, between 15% and 45%, between 20% and 35% dissolved oxygen.

Step c)

Step c) refers to a step in which the *Bordetella* is grown in the absence of the at least one bvg modulating condition of step b). In general the presence of the bvg modulating condition of step b) is removed, for example if the bvg modulating condition is a temperature lower than 28° C., incubating the mature culture in the absence of the at least one bvg modulating condition involves incubating the mature culture at a temperature of greater than 28° C. Similarly if the at least one bvg modulating condition is the presence of a bvg modulator, incubating the mature culture in the absence of the at least one bvg modulating condition involves incubating the mature culture in the absence of the bvg modulator. For example if niacin is the bvg modulator, this can be added to the first culture medium for step b) and reduced in concentration (such that it is below the modulatory concentration) in the second culture medium for step c).

In general, step c) need not occur directly after step b), there may be a gap for several days or weeks, for example in the situation where cell banking is carried out weeks or months before the cells are actually used in a fermentation. Optionally step c) does occur directly after step b).

Step b) may occur in the presence of more than one bvg modulating condition. In this case at least one, preferably all, of these bvg modulating conditions should be removed during step c).

The *Bordetella* species generally expresses a higher level of virulence factors in step c) which can be purified for use in an immunogenic composition or vaccine. At least part of step c) is generally carried out in a fermentor, although step c) may be carried out in any appropriate vessel. In one embodiment the fermentor working volume is between 5 and 10000 liters, between 10 and 5000 liters, between 20 and 2000 liters, between 50 liters and 1000 liters, greater than or equal to 5 liters, greater than or equal to 10 liters, greater than or equal to 15 liters, greater than or equal to 20 liters, greater than or equal to 25 liters, greater than or equal to 50 liters, greater than or equal to 100 liters, less than or equal to 10000 liters, less than or equal to 5000 liters or less than or equal to 2500 liters.

Step c) can be a fed-batch process. In a fed-batch process new medium is continually added to the fermentor. In one embodiment step c) is less than or equal to 100 hours, less than or equal to 80 hours, less than or equal to 60 hours, less than or equal to 40 hours, more than or equal to 5 hours, more than or equal to 10 hours, more than or equal to 15 hours, more than or equal to 25 hours between 5 hours and 100 hours, between 10 hours and 80 hours, between 15 hours and 60 hours, between 25 hours and 40 hours.

Optionally less than or equal to 20%, less than or equal to 18%, less than or equal to 15%, less than or equal to 12%, less than or equal to 10%, less than or equal to 8%, less than or equal to 6%, less than or equal to 5%, less than or equal to 4%, less than or equal to 3%, more than or equal to 1%, more than or equal to 2%, more than or equal to 3%, between 2% and 10%, between 2% and 8%, between 2% and 12%, between 2% and 10%, between 2% and 6% or between 2% and 5% of the mature culture is bvg– at the beginning of step c) or at the end of step b).

Step c) can be carried out at a temperature greater than or equal to 32° C., greater than or equal to 33° C., greater than or equal to 34° C., greater than or equal to 35° C., less than or equal to 45° C., less than or equal to 42° C., less than or equal to 40° C., less than or equal to 38° C., between 32° C. and 45° C., between 33° C. and 42° C., between 34° C. and 40° C. or between 35° C. and 38° C.

Optionally a mechanical foam breaker is used in step c).

In one embodiment step c) is less than or equal to 200 hours, less than or equal to 150 hours 100 hours, less than or equal to 80 hours, less than or equal to 60 hours, less than or equal to 40 hours, more than or equal to 5 hours, more than or equal to 10 hours, more than or equal to 15 hours, more than or equal to 25 hours between 5 hours and 200 hours, between 10 hours and 150 hours, between 15 hours and 100 hours or between 25 hours and 80 hours. In one embodiment step c) comprises incubating the mature culture in a second environment/second culture medium for at least 5, 6, 7, 8, 9, 10, 12, 15, 18, 20 generations or less than 200, 175, 150 or 125 generations.

In one embodiment step c) is carried out at a pH between 6.5 and 7.8, between 6.8 and 7.5, between 6.9 and 7.3 or between 7.0 and 7.2.

In one embodiment step c) is carried out in the presence of between 10% and 50%, between 15% and 45%, between 20% and 35% dissolved oxygen.

BVG Modulating Conditions

Any bvg modulating condition can be used in the context of the present invention. Some examples are provided below.

In one embodiment the at least one bvg modulating condition comprises incubating the sample at a temperature below or equal to 28° C., below or equal to 27° C., below or equal to 26° C., below or equal to 25° C., above or equal to 18° C., above or equal to 20° C., above or equal to 22° C., above or equal to 24° C., between 0° C. and 28° C., between 0° C. and 27° C., between 0° C. and 26° C. or between 0° C. and 25° C.

In one embodiment the at least one bvg modulating condition comprises incubating the sample at an oxygen concentration below or equal to 0.100, below or equal to 0.090, below or equal to 0.080, below or equal to 0.070, above or equal to 0.001, above or equal to 0.050, above or equal to 0.010, above or equal to 0.015, above or equal to 0.020, above or equal to 0.025, between 0.010 and 0.100, between 0.010 and 0.090, between 0.010 and 0.080 or between 0.010 and 0.070 mmol dissolved $O_2$ per liter.

In one embodiment the at least one bvg modulating condition comprises incubating the sample at a basic pH. Optionally the pH is a pH greater than or equal to 7.2, greater than or equal to 7.3, greater than or equal to 7.4, less than or equal to 9.5, less than or equal to 9.0, less than or equal to 8.5, less than or equal to 8.0, between 7.2 and 8.0, between 7.3 and 8.0 or between 7.4 and 8.0.

In one embodiment the at least one bvg modulating condition comprises incubating the sample at an acidic pH. Optionally the acidic pH is a pH less than or equal to 7.0, less than or equal to 6.8, less than or equal to 6.6, less than or equal to 6.4, less than or equal to 6.2, above or equal to 4.5, above or equal to 5.0, above or equal to 5.5, above or equal to 6.0, above or equal to 6.5, between 5.0 and 7.0, between 5.0 and 6.9 or between 5.0 and 6.8.

In one embodiment the at least one bvg modulator comprises niacin. Optionally the bvg modulator comprises niacin at a concentration of greater than or equal to 0.004 g/l, greater than or equal to 0.01 g/l, greater than or equal to 0.1 g/l, greater than or equal to 0.2 g/l greater than or equal to 0.3 g/l, greater than or equal to 0.004 g/l, less than or equal to 400 g/l, less than or equal to 300 g/l, less than or equal to 200 g/l, less than or equal to 100 g/l, less than or equal to 50 g/l, less than or equal to 5 g/l, between 0.004 g/l and 500 g/l, between 0.01 g/l and 400 g/l, between 0.1 g/l and 300 g/l, between 0.4 g/l and 200 g/l or between 0.2 g/l and 100 g/l.

In one embodiment the at least one bvg modulator comprises an inorganic salt selected from the group consisting of a magnesium salt, a sulphate salt, a phosphate salt and a carbonate salt. Optionally the inorganic salt is a sulphate salt. The sulphate salt can be at a concentration of greater than or equal to 0.04 mM, greater than or equal to 0.08 mM, greater than or equal to 1 mM, greater than or equal to 4 mM, greater than or equal to 8 mM, greater than or equal to 10 mM, less than or equal to 50 mM, less than or equal to 40 mM, less than or equal to 35 mM, less than or equal to 30 mM, less than or equal to 25 mM, less than or equal to 20 mM, less than 15 mM, between 0.04 mM and 40 mM, between 0.08 mM and 1 mM, between 4 mM and 40 mM, between 8 mM and 10 mM, between 15 mM and 40 mM, or between 17 mM and 40 mM.

Optionally the inorganic salt is a phosphate salt. The phosphate salt can be at a concentration of greater than or equal to 0.4 g/l, greater than or equal to 0.5 g/l, greater than or equal to 0.6 g/l, greater than or equal to 0.7 g/L, less than or equal to 20 g/l, less than or equal to 18 g/l, less than or equal to 16 g/l, less than or equal to 10 g/l, less than or equal to 5 g/l, less than or equal to 2 g/l, between 0.4 g/L and 20 g/L, between 0.5 g/L and 20 g/L, between 0.6 g/L and 20 g/L or between 0.7 g/L and 20 g/L.

In one embodiment the at least one bvg modulator comprises sucrose. The sucrose can be at a concentration of greater than or equal to 10 mM, greater than or equal to 15 mM, greater than or equal to 20 mM, greater than or equal to 25 mM, greater than or equal to 30 mM, greater than or equal to 35 mM, greater than or equal to 40 mM, less than or equal to 100 mM, less than or equal to 90 mM, less than or equal to 85 mM, less than or equal to 80 mM, less than or equal to 75 mM, less than or equal to 70 mM, less than or equal to 50 mM, between 10 mM and 100 mM, between 15 mM and 95 mM, between 20 mM and 90 mM, between 25 mM and 85 mM or between 30 mM and 80 mM.

Optionally the at least one bvg modulator comprises a complex medium component selected from the group consisting of yeast extract, tryptic soy agar, tryptose phosphate, peptones and infusions of brain and heart tissue and peptones. The complex medium component can be at a concentration of greater than or equal to 1 g/L, greater than or equal to 3 g/L, greater than or equal to 5 g/L, greater than or equal to 10 g/L, less than or equal to 40 g/L, less than or equal to 35 g/L, less than or equal to 30 g/l, less than or equal to 25 g/l, less than or equal to 20 g/L, between 1 g/L and 40 g/l, between 3 g/l and 40 g/l, between 5 g/l and 40 g/L, or between 10 g/L and 40 g/L.

Optionally the at least one bvg modulator comprises proline. The proline can be at a concentration of greater than or equal to 0.25 g/l, greater than or equal to 0.4 g/l, greater than or equal to 0.5 g/l, greater than or equal to 0.6 g/L, greater than or equal to 1 g/L, greater than or equal to 2 g/L, greater than or equal to 3 g/L greater than or equal to 4 g/l, less than or equal to 50 g/L, less than or equal to 30 g/L, less than or equal to 25 g/L, less than or equal to 20 g/L, less than or equal to 15 g/L, between 0.25 g/L an 50 g/L, between 0.4 g/L and 50 g/L, between 0.5 g/L and 50 g/L, between 0.6 g/L and 50 g/L, between 1 g/L and 50 g/L, between 2 g/L and 50 g/L, between 3 g/L and 50 g/L, or between 4 g/L and 50 g/L.

In one embodiment the at least one bvg modulator comprises sodium ions at a concentration greater than 100 mM, greater than 120 mM, greater than 150 mM, greater than 175 mM, greater than 200 mM, greater than 250 mM, less than 2000 mM, less than 1000 mM, less than 800 mM, between 100 mM and 2000 mM, between 120 mM and 2000 mM, between 150 mM and 2000 mM, between 175 mM and 2000 mM, or between 200 mM and 2000 mM.

In one embodiment the bvg modulator comprises an antifoaming agent. Optionally the antifoaming agent is Polydimethylsiloxane. The Polydimethylsiloxane can be at a concentration of greater than or equal to 5 g/l, greater than or equal to 10 g/l, greater than or equal to 15 g/l, greater than or equal to 20 g/l, greater than or equal to 25 g/l, greater than or equal to 30 g/l, greater than or equal to 40 g/l, less than or equal to 250 g/l, less than or equal to 230 g/l, less than or equal to 200 g/l, less than or equal to 180 g/l, less than or equal to 150 g/l between 5 g/l and 250 g/l, between 10 g/l and 230 g/l, between 15 g/l and 200 g/l, between 20 g/l and 180 g/l, between 25 g/l and 150 g/l or between 25 g/l and 150 g/l.

In one embodiment the at least one bvg modulator comprises glutathione. The glutathione can be at a concentration greater than or equal to 0.15 g/L, greater than or equal to 0.20 g/L, greater than or equal to 0.25 g/L, greater than or equal to 0.30 g/L, greater than or equal to 0.35 g/L, greater than or equal to 0.40 g/L, less than or equal to 20 g/L, less than or equal to 15 g/l, less than or equal to 12 g/L, less than or equal to 10 g/L, between 0.15 g/L and 20 g/L, between 0.20 g/L and 20 g/L, between 0.25 g/L and 20 g/L, between 0.30 g/L and 20 g/L, between 0.35 g/L and 20 g/L, between 0.35 g/L and 20 g/L or between 0.40 g/L and 20 g/L.

In one embodiment the at least one bvg modulator comprises a sulphur containing amino acid, these amino acids include, Cysteine, Cystine, Methionine, but also includes any further amino acids which contain a sulphur atom (both natural and non-natural amino acids). These amino acids may be derived from a protein or peptide source or may be sourced as individual amino acids. In a further embodiment the at least one bvg modulator comprises a sulphur containing amino acid at a concentration of greater than or equal to 0.25 mM, greater than or equal to 0.5 mM, greater than or equal to 0.8 mM, less than or equal to 1000 mM, less than or equal to 500 mM, less than or equal to 250 mM, less than or equal to 100 mM, less than or equal to 50 mM, less than or equal to 25 mM, less than or equal to 10 mM, between 0.25 mM and 1000 mM, between 0.5 mM and 500 mM, between 0.8 mM and 250 mM, or between 0.5 mM and 100 mM.

Further Steps

In one embodiment the *Bordetella* species expresses at least one virulence factor selected from the group consisting of *Pertussis* Toxin, Filamentous Haemagglutinin, fimbrial aggultinogen and Pertactin. Optionally the *Pertussis* Toxin is produced at a specific *Pertussis* Toxin production rate less than 2.8 $mgL^{-1}$ $OD_{650\ nm}{}^{-1}$, 2.7 $mgL^{-1}$ $OD_{650\ nm}{}^{-1}$, 2.6 $mgL^{-1}$ $OD_{650\ nm}{}^{-1}$, 2.5 $mgL^{-1}$ $OD_{650\ nm}{}^{-1}$, 2.4 $mgL^{-1}$ $OD_{650\ nm}{}^{1}$, 2.3 $mgL^{-1}$ $OD_{650\ nm}{}^{-1}$, 2.2 $mgL^{-1}$ $OD_{650\ nm}{}^{-1}$, 2.1 $mgL^{-1}$ $OD_{650\ nm}{}^{-1}$, 2.0 $mgL^{-1}$ $OD_{650\ nm}{}^{-1}$ 1.9 $mgL^{-1}$, $OD_{650\ nm}{}^{-1}$, 1.8 $mgL^{-1}$ $OD_{650\ nm}{}^{-1}$, 1.7 $mgL^{-1}$ $OD_{650\ nm}{}^{-1}$, or 1.6 $mgL^{-1}$ $OD_{650\ nm}{}^{-1}$ in step b). Optionally the *Pertussis* Toxin is produced at a specific *Pertussis* Toxin production rate greater than 8 $mgL^{-1}{}_{650\ nm}{}^{-1}$, 2.9 $mgL^{-1}{}_{650\ nm}{}^{-1}$, 3.0 $mgL^{-1}{}_{650\ nm}{}^{-1}$, 3.1 $mgL^{-1}{}_{650\ nm}{}^{-1}$ or 3.2 $mgL^{-1}{}_{650\ nm}{}^{-1}$ during step c).

The process of the disclosure can include a further step d) of purifying the virulence factor to produce a purified virulence factor. The purified virulence factor can be a purified *Pertussis* Toxin (PT), Filamentous Haemagglutinin (FHA), Pertactin (PRN), agglutinogen 2 or agglutinogen 3. The purified virulence factor can be altered after purification, for example *Pertussis* Toxin can be chemically detoxified after purification. See also EP 427462 and WO 91/12020 for the preparation of *pertussis* antigens. In one embodiment a step d) involves cell purification using chromatography. In one embodiment the chromatography technique is affinity chromatography, gel filtration, high pressure liquid chromatography (HPLC) or ion exchange chromatography. Optionally the affinity chromatography uses an affinity tag purification column, an antibody purification column, a lectin affinity column, a prostaglandin purification column or a strepavidin column. Optionally the HPLC uses an ion exchange column, a reverse phase column or a size exclusion column. Optionally the ion exchange column is an anion exchange column or a cation exchange column.

The process can further comprise a step e) of formulating an immunogenic composition comprising the purified virulence factor.

The process can further comprise a step f) of adding at least one further antigen to the immunogenic composition. In one embodiment the at least one further antigen is selected from the group consisting of Pertussis Toxin, Filamentous Haemaglutinin, Pertactin, a Fimbrial Agglutinogen, Diphtheria Toxoid, Tetanus Toxoid, at least one conjugated saccharide antigen from N. meningitidis, Hepatitis B surface antigen, Inactivated Polio Virus (IPV) and a conjugated saccharide antigen from Haemophilus influenzae b. The at least one conjugated saccharide antigen from N. meningitidis can be MenC, MenY, MenA and MenW (e.g. A+C, A+Y, A+W, C+Y, C+W, Y+W, A+C+Y, A+C+W, A+Y+W, C+Y+W, A+C+Y+W); optionally MenC and/or MenY is included optionally all four are included.

Alternatively or in addition to the above meningococcal antigens, the immunogenic composition can comprise one or more pneumococcal capsular oligosaccharide or polysaccharide—carrier protein conjugates.

Typically pneumococcal capsular oligosaccharides or polysaccharides (preferably the latter) represented in the compositions of the invention comprise antigens derived from at least four serotypes of pneumococcus. Preferably the four serotypes comprise 6B, 14, 19F and 23F. More preferably, at least 7 serotypes are comprised in the composition, for example those derived from serotypes 4, 6B, 9V, 14, 18C, 19F, and 23F. More preferably still, at least 11 serotypes are comprised in the composition (11 valent), for example those derived from serotypes 1, 3, 4, 5, 6B, 7F, 9V, 14, 18C, 19F and 23F. More preferably still, at least 10 serotypes are comprised in the composition (10 valent), for example those derived from serotypes 1, 4, 5, 6B, 7F, 9V, 14, 18C, 19F and 23F. In a preferred embodiment of the invention at least 13 of such conjugated pneumococcal antigens are comprised, although further antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

In one embodiment the immunogenic composition comprises a pharmaceutically acceptable excipient. In one embodiment the fermentation process comprises a step g) of adding a pharmaceutically acceptable excipient to the immunogenic composition.

In one embodiment the immunogenic composition comprises an adjuvant such as aluminium phosphate or aluminium hydroxide. In one embodiment the fermentation process comprises a step f) of adding an adjuvant to the immunogenic composition. Methods of adsorbing DTPa and DTPw antigens onto aluminium adjuvants are known in the art. See for example WO 93/24148 and WO 97/00697. Usually components adsorbed onto adjuvant are left for a period of at least 10 minutes at room temperature at an appropriate pH for adsorbing most and preferably all of the antigen before mixing the antigens together in the combination immunogenic compositions of the present invention.

Other components are preferably unadsorbed (such as IPV) or adsorbed specifically onto other adjuvants—Hepatitis B surface antigen (HBsAg) being preferably adsorbed onto aluminium phosphate (as described in WO 93/24148) before mixing with other components.

In a further embodiment there is provided a virulence factor obtainable by the process. In a further embodiment there is provided a virulence factor obtained by the process.

In a further embodiment there is provided an immunogenic composition comprising the virulence factor and a pharmaceutically acceptable excipient. In one embodiment the immunogenic composition comprises at least one further antigen. In one embodiment the at least one further antigen is selected from the group consisting of Pertussis Toxin, Filamentous Haemaglutinin, Pertactin, a Fimbrial Agglutinogen, Diphtheria Toxoid, Tetanus Toxoid, at least one conjugated saccharide antigen from N. meningitidis, Hepatitis B surface antigen, Inactivated Polio Virus (IPV) and a conjugated saccharide antigen from Haemophilus influenzae b (optionally conjugated to Tetanus Toxoid). The at least one conjugated saccharide antigen from N. meningitidis can be MenC, MenY, MenA and MenW (e.g. A+C, A+Y, A+W, C+Y, C+W, Y+W, A+C+Y, A+C+W, A+Y+W, C+Y+W, A+C+Y+W); optionally MenC and/or MenY is included optionally all four are included. In one embodiment the vaccine comprises diphtheria toxoid, tetanus toxoid, and at least one of PT, FHA and PRN (a DTPa vaccine).

In one embodiment the immunogenic composition further comprises an adjuvant. In one embodiment the immunogenic composition comprises aluminium phosphate or aluminium hydroxide. Methods of adsorbing DTPa antigens onto aluminium adjuvants are known in the art. See for example WO 93/24148 and WO 97/00697. Usually components adsorbed onto adjuvant are left for a period of at least 10 minutes at room temperature at an appropriate pH for adsorbing most and preferably all of the antigen before mixing the antigens together in the combination immunogenic compositions of the present invention.

Other components are preferably unadsorbed (such as IPV) or adsorbed specifically onto other adjuvants—Hepatitis B surface antigen (HBsAg) being preferably adsorbed onto aluminium phosphate (as described in WO 93/24148) before mixing with other components.

In one embodiment there is a provided a vaccine comprising the immunogenic composition.

Vaccine preparation is generally described in Vaccine Design—The Subunit and adjuvant approach Ed Powell and Newman; Pellum Press. Advantageously the combination vaccine according to the invention is a paediatric vaccine.

The amount of polysaccharide or oligosaccharide conjugate antigen in each vaccine dose is selected as an amount which induces an immunoprotective response without significant, adverse side effects in typical vaccinees. Such amount will vary depending on which specific immunogens are employed. Generally it is expected that each dose will comprise 1-1000 µg of conjugated polysaccharide or oligosaccharide (expressed in amount of saccharide), preferably 2-100 µg, more preferably 4-40, 2-15, or 3-10 µg, most preferably around or exactly 5 µg.

The content of protein antigens in the vaccine will typically be in the range 1-100 µg, preferably 5-50 µg, most typically in the range 5-25 µg.

An optimal amount of antigen for a particular vaccine can be ascertained by standard studies involving observation of antibody titres and other responses in subjects. Following an initial vaccination, subjects can receive one or two booster injections at about 4 weeks intervals or longer.

The vaccine preparations of the present invention can be used to protect or treat a mammal (preferably human) susceptible to infection, by means of administering said vaccine via systemic or mucosal route. These administrations can include injection via the intramuscular, intraperitoneal, intradermal or subcutaneous routes.

In a further aspect there is provided the immunogenic composition or the vaccine as previously described for use in the prevention or treatment of disease.

In a further aspect there is provided the immunogenic composition or the vaccine as previously described for use in the prevention or treatment of Bordetella pertussis disease.

In a further aspect there is provided a use of the immunogenic composition or the vaccine as previously described in the prevention or treatment of disease.

In a further aspect there is provided a use of the immunogenic composition or the vaccine as previously described in the preparation of a medicament for the treatment or prevention of bacterial disease.

In a further aspect there is provided a method of preventing or treating disease comprising administering the immunogenic composition or the vaccine as previously described to a patient.

In one embodiment the disease is Bordetella pertussis disease.

EXAMPLES

Example 1

Growth and Virulence Factor Production by Bordetella pertussis bvg$^+$ and bvg$^-$ Mutants in 20 L-Scale Fermentation A shake flask culture of B. pertussis was plated on Bordet-Gengou medium (containing 5% sheep blood), in order to be able to detect haemolytic (bvg$^+$) and non-haemolytic (bvg$^-$) colonies. One single bvg$^+$ colony and one single bvg$^-$ colony were isolated from these plates, and used to perform 20 L-scale fermentations.

A first shake-flask pre-culture containing 7.5 ml fresh medium (adapted from Stainer and Scholte (J. Gen. Microbiol. 63:211-220 (1971)) by the addition of dimethyl-cyclodextrin 1 g/L and acid casein hydrolysate 10 g/L, the replacement of L-cystine 40 mg/L with L-cysteine 40 mg/L, and the use of higher concentrations of Na-L-Glutamate (11.84 g/L), reduced glutathione (150 mg/L) and ascorbic acid (400 mg/L)) was inoculated with $10^9$ B. pertussis CFUs and incubated at 35° C. (+/−1° C.) and 150 rpm for 24 h (+/−1 h) to produce a first pre-culture. The first pre-culture was used to inoculate a second shake-flask pre-culture containing 100 ml fresh medium. The second pre-culture was incubated at 35° C. (+/−1° C.) and 150 rpm for 24 h (+/−1 h), and used to inoculate two shake flasks each containing 1 L fresh medium. After growth at 35° C. (+/−1° C.) and 150 rpm for 24 h (+/−4 h), the two shake-flasks from the third pre-culture were pooled. The pooled pre-culture was used to inoculate a fermentor as soon as the third pre-culture was stopped. In parallel, the proportion of bvg$^+$ and bvg$^-$ cells at the end of the third pre-culture was measured by plating appropriate dilutions on BG (Bordet Gengou) medium (containing 5% blood). This proportion represented the initial proportion of bvg$^-$ cells in the 20 L-fermentation (Table 1).

A 20 L-fermentor (Biolafitte™) was used. 10 L of medium were aseptically transferred into the fermentor. The following conditions were used in order to calibrate the 100%-dissolved oxygen (DO) level: temperature (35° C.), head pressure (0.4 bar), air flow rate (4.6 L sparged air per minute) and stirring speed (50 rpm or rotations per minute).

Inoculation was achieved by the addition of 1.5 L of the pooled pre-culture.

During the fermentation, the temperature (35° C.) and head pressure (0.4 bar) were maintained at a constant level. A mechanical foam breaker was used to control foaming during the fermentation. The air flow rate was progressively increased during the fermentation, according to a pre-defined curve. The level of dissolved oxygen was set at 25% and regulated by increasing stirring when the DO fell below 25%. The minimum stirring speed was set at 50 rpm; the maximum stirring speed was set at 550 rpm. The pH was regulated at 7.2 by addition of acetic acid 50% (w/v or weight/volume).

Figure 1:
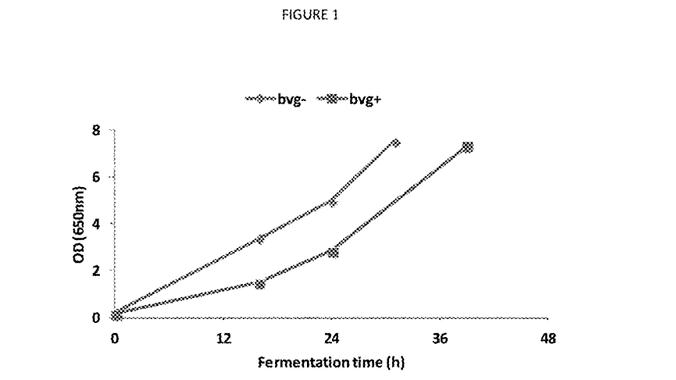
FIG. 1. Graph depicting growth of bvg$^-$ genotype and bvg$^+$ genotype *Bordetella pertussis* cells against fermentation time. Growth of the bvg$^-$ cells is depicted by the line connecting diamond shaped points; growth of the bvg$^+$ cells is depicted by the line connecting the square shaped points.

During the fermentation, growth of the bvg− and bvg+ cultures was monitored as optical density at 650 nm ($OD_{650\,nm}$; FIG. 1). At the end of fermentation (defined as the time at which oxygen consumption decreases—as a consequence of glutamate exhaustion—, resulting in a decrease in stirring speed), pertussis toxin (PT) production in the culture supernatant was determined by standard ELISA, and the proportion of bvg$^+$ and bvg$^-$ cells was measured by plating appropriate dilutions of fermentation broth on BG medium containing 5% blood (Table 1). This proportion represented the final proportion of bvg$^-$ cells in the 20 L-fermentation (Table 1).

Fermentation with the bvg$^-$ isolate resulted in faster growth, but very low PT production, compared to fermentation with the bvg$^+$ isolate. However, the maximum biomass concentration was not different between the two isolates.

TABLE 1

Main fermentation parameters for 20 L-fermentations of B. pertussis bvg$^+$ and bvg$^-$ isolates;

|  | COQ261 | COQ262 |
|---|---|---|
| Single colony isolate | bvg$^-$ | bvg$^+$ |
| Initial proportion of bvg$^-$ in 20 L-fermentor | 100% | 1% |
| Total fermentation time* | 31 h | 39 h |
| Maximum biomass ($OD_{650\,nm}$) | 7.5 | 7.3 |
| Final proportion of bvg$^-$ in 20 L-fermentor | 100% | 0% |
| PT concentration at end of fermentation | 5.5 mg/L | 22.3 mg/L |

*The total fermentation time is defined as the time at which oxygen consumption decreases (as a consequence of glutamate exhaustion), resulting in a decrease in stirring speed.

Example 2

Accumulation of bvg$^-$ Cells in a 20 L-Scale Fermentation of Bordetella pertussis A 20 L-fermentation of Bordetella pertussis was performed as described in example 1, except that the first pre-culture was inoculated with $10^9$ B. pertussis CFUs representing a 99:1 ratio of bvg$^+$ to bvg$^-$ cells.

The proportion of bvg$^+$ and bvg$^-$ cells was measured at the start and at the end of the 20 L-fermentation, by plating appropriate dilutions of the fermentation broth on BG medium containing 5% blood (Table 2). The proportion of bvg- cells increased as the number of generations increased.

TABLE 2

Main fermentation parameters for 20 L-fermentations of B. pertussis bvg+ and bvg- isolates.

|  | COQ238 |
| --- | --- |
| Initial proportion of bvg- in first pre-culture | 1% |
| Initial proportion of bvg- in 20 L-fermentor | 5% |
| Total fermentation time* | 35 h |
| Maximum biomass ($OD_{650\ nm}$) | 6.9 |
| Final proportion of bvg- in 20 L-fermentor | 20% |

*The total fermentation time is defined as the time at which oxygen consumption decreases (as a consequence of glutamate exhaustion), resulting in a decrease in stirring speed.

Example 3

Effect of Modulating Compounds on the Take-Over of bvg- Cells During Serial Shake-Flask Cultures Four series of cultures were performed in parallel in medium adapted from Stainer and Scholte (J. Gen. Microbiol. 63:211-220 (1971)) with the modifications described in example 1, each series containing $MgSO_4$ (10 mM) and/or niacin (0 g/L or 0.604 g/L), as described in Table 3. For each series, the first shake-flask containing 7.5 ml fresh medium was inoculated with $10^9$ B. pertussis CFUs representing a 99:1 ratio of bvg+ to bvg- cells. All subsequent shake-flask cultures contained 100 ml fresh medium. All cultures were incubated for 24 h (+/−1 h) at 35° C. (+/−1° C.). At the end of the third and fourth passages, the proportion of bvg+ and bvg- cells was measured by plating appropriate dilutions of the culture on BG medium containing 5% blood (Table 3).

In the absence of modulating concentrations of $MgSO_4$ or niacin (series A), bvg- cells accumulated rapidly. The addition of either $MgSO_4$ (20 mM; series C) or niacin (0.604 g/L; series B) or both resulted in a significantly lower accumulation of bvg- cells.

TABLE 3

Effect of the modulating compounds $MgSO_4$ and niacin on the take-over of bvg- cells during serial shake-flask cultures.

|  | Series A | Series B | Series C | Series D |
| --- | --- | --- | --- | --- |
| $MgSO_4$ | — | — | 20 mM | 20 mM |
| Niacin | 0.004 g/L | 0.604 g/L | 0.004 g/L | 0.604 g/L |
| Proportion of bvg- cells |  |  |  |  |
| Start of first culture | 1% | 1% | 1% | 1% |
| End of third culture | 5% | 1% | 3% | 0% |
| End of fourth culture | 8% | 2% | 2% | 2% |

Example 4

Figure 2:
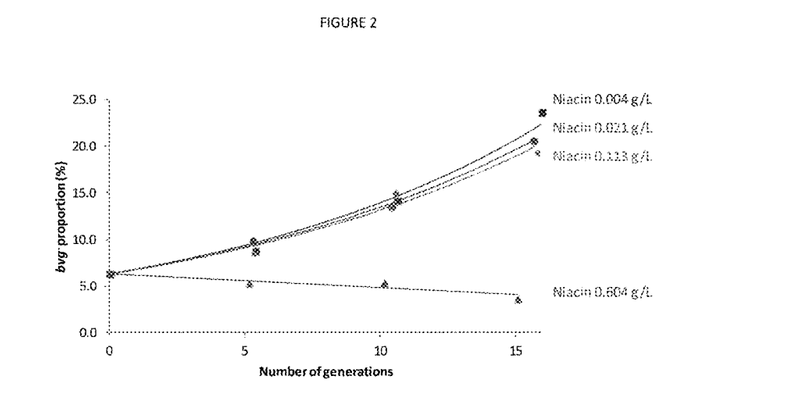
FIG. 2. Graph depicting the proportion of *Bordetella pertussis* cells which are bvg$^-$ genotype against number of generations with varying levels of the bvg modulator niacin. The line connecting the square shaped points depicts the proportion of the cells which are bvg$^-$ when 0.004 g/L of niacin is used, the line connecting the circle shaped points depicts the proportion of cells which are bvg$^-$ genotype when 0.021 g/L of niacin is used, the line connecting the diamond shaped points depicts the proportion of cells which are bvg$^-$ when 0.113 g/L of niacin is used and the line connecting the triangular shaped points depicts the proportion of cells which are bvg$^-$ when 0.604 g/L of niacin is used.

Dose Effect of the Modulating Compound Niacin on the Take-Over of bvg- Cells During Serial Shake-Flask Cultures The dose effect of niacin on the take-over of bvg- cells was evaluated during serial shake-flask cultures of *Bordetella pertussis*. Four series of cultures were performed in parallel in medium adapted from Stainer and Scholte (J. Gen. Microbiol. 63:211-220 (1971)), with the modifications described in example 1. Medium also contained the following modifications: replacement of the acid casein hydrolysate with a mixture of 12 amino acids (L-Aspartate, Glycine, L-Valine, L-Methionine, L-Isoleucine, L-Leucine, L-Phenylalanine, L-Histidine, L-Alanine, L-Tyrosine, L-Serine, and L-Lysine) in concentrations equivalent to those obtained with 10 g/L casein hydrolysate, increased Na-L-Glutamate (20 g/L) and L-Proline (1.04 g/L) concentrations, and absence of NaCl. Each series contained different concentrations of niacin, as described in Table 4. For each series, the first shake-flask containing 100 ml fresh medium was inoculated with approximately $4\times10^9$ B. pertussis CFUs representing a 94:6 ratio of bvg+ to bvg- cells. All subsequent shake flasks contained 100 ml fresh medium, and were inoculated with the preceding culture at an initial cell concentration of approximately $4\times10^8$ CFU/ml. All cultures were incubated for 24 h (+/−1 h) at 35° C. (+/−1° C.) and 150 rpm. At the end of each passage, the proportion of bvg+ and bvg- cells was measured by plating appropriate dilutions of the culture on BG medium containing 5% blood (Table 4). The number of generations at each passage was calculated based on optical density measurements ($OD_{650\ nm}$). The take-over of bvg- cells as a function of the number of generations is depicted in FIG. 2.

Low niacin concentrations were less effective in controlling the take-over of bvg- cells. However, when niacin was added at a high concentration (0.604 g/L), no bvg- take-over was observed, up to 15 generations.

TABLE 4

Dose effect of the modulating compound niacin on the take-over of bvg- cells during serial shake-flask cultures.

|  | Series A | Series B | Series C | Series D |
| --- | --- | --- | --- | --- |
| Niacin | 0.004 g/L | 0.021 g/L | 0.113 g/L | 0.604 g/L |
| Proportion of bvg- cells |  |  |  |  |
| Start of first culture | 6% | 6% | 6% | 6% |
| End of first culture | 9% | 9% | 10% | 5% |
| End of second culture | 14% | 15% | 14% | 5% |
| End of third culture | 24% | 19% | 21% | 4% |

Example 5

Use of the Modulating Compound Niacin to Control the Take-Over of bvg- Cells in 20 L-Scale Fermentation Two 20 L-fermentations of *B. pertussis* were performed in parallel. The two fermentations were identical, except for the presence of a high niacin concentration (0.604 g/L) in the first two pre-cultures of fermentation COQ255, in order to control bvg- take-over, while the next two pre-cultures of fermentation COQ255 contained a low niacin concentration (0.004 g/L). In fermentation COQ254, all four pre-cultures were performed in the presence of 0.004 g/L niacin. The niacin concentration at each step of the process is indicated in Table 5. Due to the medium dilution at each pre-culture step, the initial niacin concentration in the 20 L-fermentor was 0.004 g/L, i.e. below the modulating concentration, allowing PT production.

TABLE 5

Initial niacin concentration at each step of the fermentation process for B. pertussis fermentations with (COQ255) or without (COQ254) control of bvg⁻ take-over at the pre-culture step.

|  | COQ254 | COQ255 |
|---|---|---|
| Added niacin concentration* | | |
| First pre-culture | 0.004 g/L | 0.604 g/L |
| Second pre-culture | 0.004 g/L | 0.604 g/L |
| Third pre-culture | 0.004 g/L | 0.004 g/L |
| Fourth pre-culture | 0.004 g/L | 0.004 g/L |
| 20 L-fermentor | 0.004 g/L | 0.004 g/L |
| Effective niacin concentration** | | |
| First pre-culture | 0.004 g/L | 0.596 g/L |
| Second pre-culture | 0.004 g/L | 0.604 g/L |
| Third pre-culture | 0.004 g/L | 0.022 g/L |
| Fourth pre-culture | 0.004 g/L | 0.005 g/L |
| 20 L-fermentor | 0.004 g/L | 0.004 g/L |

*Represents the niacin concentration in the fresh medium.
**Represents the calculated niacin concentration, taking into account the niacin concentration in the fresh medium, the dilution of the fresh medium due to the addition of the inoculum, and the niacin brought along with the inoculum from the previous step (assuming no niacin utilization or degradation during growth).

The same frozen cell bank was used to inoculate the first pre-cultures of both fermentations, consisting of a shake-flask containing 30 ml of fresh medium (adapted from Stainer and Scholte (J. Gen. Microbiol. 63:211-220 (1971)), with the modifications described in example 1) with approximately $1 \times 10^9$ B. pertussis CFUs representing a 99:1 ratio of bvg⁺ to bvg⁻ cells. The first pre-culture was incubated at 35° C. (+/−1° C.) and 150 rpm for 24 h (+/−1 h), and used to inoculate a second shake-flask pre-culture containing 1 L fresh medium. The second pre-culture was incubated at 35° C. (+/−1° C.) and 150 rpm for 24 h (+/−2 h), and used to inoculate a third shake flask containing 1 L fresh medium. After incubation at 35° C. (+/−1° C.) and 150 rpm for 24 h (+/−1 h), the third pre-culture was used to inoculate two shake-flasks each containing 1 L fresh medium. After growth at 35° C. (+/−1° C.) and 150 rpm for 13 h (+/−1 h), the two shake-flasks from the fourth pre-culture were pooled. The pooled pre-culture was used to inoculate a fermentor as soon as the fourth pre-culture was stopped. In parallel, the proportion of bvg⁺ and bvg⁻ cells at the end of the fourth pre-culture was measured by plating appropriate dilutions on BG containing 5% blood medium. This proportion represented the initial proportion of bvg cells in the 20 L-fermentation (Table 6). The number of generations of the pre-culture train (18 generations, as calculated from $OD_{650\ nm}$ measurements) represents a number of generations which can be used to perform fermentation at commercial scale (approximately 2,000 L fermentation broth).

A 20 L-fermentor (Biolafitte) was used. 10 L of medium were aseptically transferred into the fermentor. The following conditions were used in order to calibrate the 100%-dissolved oxygen (DO) level: temperature (35° C.), head pressure (0.4 bar), air flow rate (4.6 L sparged air per minute) and stirring speed (50 rpm).

Inoculation was achieved by the addition of 1.5 L of the pooled pre-culture.

During the fermentation, the temperature (35° C.) and head pressure (0.4 bar) were maintained constant. A mechanical foam breaker was used to control foaming during the fermentation. The air flow rate was progressively increased during the fermentation, according to a pre-defined curve. The level of dissolved oxygen was set at 25% and regulated by increasing stirring when the DO fell below 25%. The minimum stirring speed was set at 50 rpm; the maximum stirring speed was set at 550 rpm. The pH was regulated at 7.2 by addition of acetic acid 50% (w/v).

During the fermentation, growth was monitored as optical density at 650 nm ($OD_{650\ nm}$). At the end of fermentation (defined as the time at which oxygen consumption decreases—as a consequence of glutamate exhaustion—, resulting in a decrease in stirring speed), pertussis toxin (PT) production in the culture supernatant was determined by ELISA, and the proportion of bvg⁺ and bvg⁻ cells was measured by plating appropriate dilutions of fermentation broth on BG medium containing 5% blood (Table 6). This proportion represented the final proportion of bvg⁻ cells in the 20 L-fermentation (Table 6).

The addition of high niacin concentration during the first two pre-culture steps resulted in a lower proportion of bvg⁻ cells at the start of the 20 L-fermentation. Although no control was exerted on bvg⁻ take-over during the fermentation itself (0.004 g/L niacin, to allow PT expression), the lower initial proportion of bvg⁻ cells was reflected at the end of fermentation, and resulted in a significant increase in PT titers in the fermentation broth. Fermentation COQ255 was slightly slower, in agreement with the observation that bvg⁻ cells grow faster than bvg⁺ cells. The final biomass concentration was similar between the two fermentations: only the composition of the bacterial population in terms of bvg⁺: bvg⁻ ratio was affected. This is illustrated by the increase in specific PT production (Table 6).

TABLE 6

Main fermentation parameters for 20 L-fermentations of B. pertussis with (COQ255) or without (COQ254) control of bvg⁻ take-over at the pre-culture step.

|  | COQ254 | COQ255 |
|---|---|---|
| Control of bvg⁻ take-over at pre-culture step | without | with |
| Initial proportion of bvg⁻ in 20 L-fermentor | 13% | 3% |
| Total fermentation time* | 40 h | 43 h |
| Final biomass ($OD_{650\ nm}$) | 6.7 | 7.2 |
| Final proportion of bvg⁻ in 20 L-fermentor | 34% | 13% |
| PT concentration at end of fermentation | 18.7 mg/L | 22.8 mg/L |
| Specific PT production at end of fermentation | 2.8 mg L⁻¹ $OD_{650\ nm}^{-1}$ | 3.2 mg L⁻¹ $OD_{650\ nm}^{-1}$ |

*The total fermentation time is defined as the time at which oxygen consumption decreases (as a consequence of glutamate exhaustion), resulting in a decrease in stirring speed.

Example 6

Low Dissolved Oxygen as a Condition that Inhibits PT Production

Figure 3:
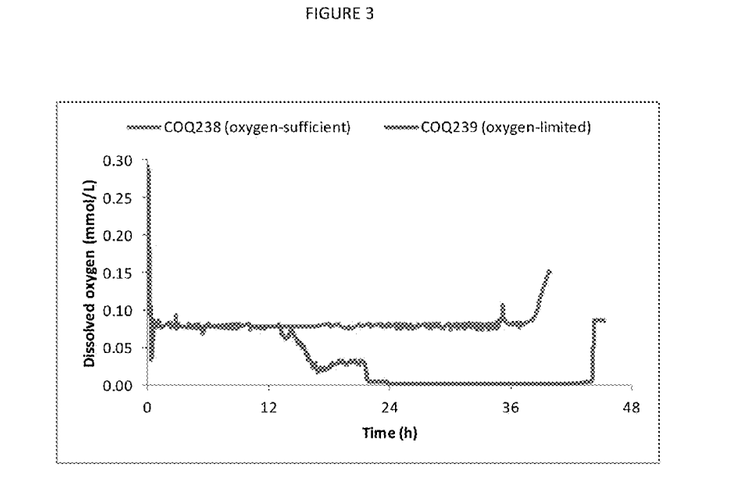
FIG. 3 Graph depicting the dissolved oxygen profile for the two fermentations described in example 6. The top line describes the dissolved oxygen profile when the fermentation was oxygen sufficient and the bottom line describes the dissolved oxygen profile when the fermentation was oxygen limited.
Figure 4:
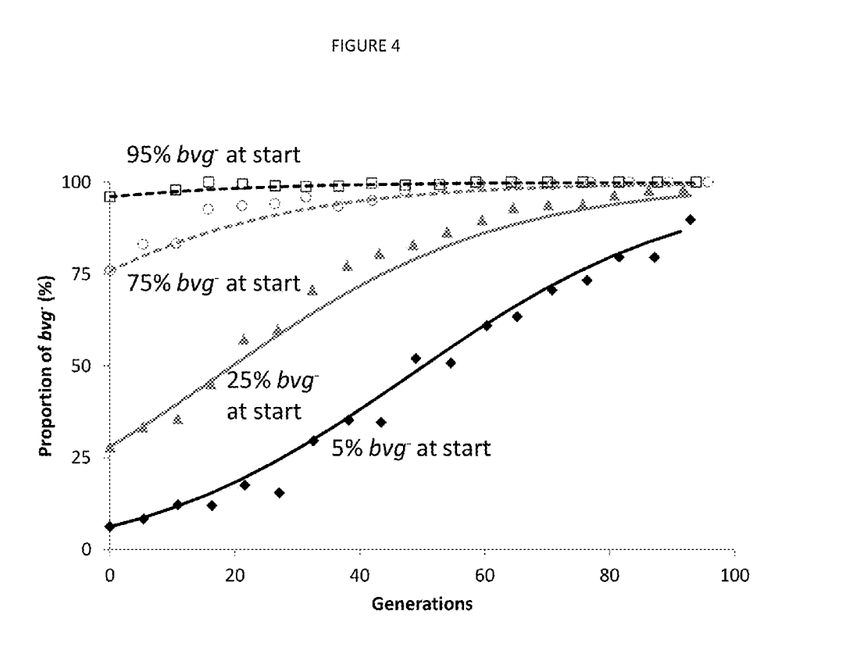
FIG. 4 Graph depicting the proportion of bvg– genotype cells in 4 cultures fermented in the presence of 0.004 g/L of niacin against number of generations. The square shaped points represent a culture with a starting proportion of 95% bvg– genotype cells at the beginning of the fermentation. The circle shaped points represent a culture with a starting proportion of 75% bvg– genotype cells at the beginning of the fermentation. The triangular shaped points represent a culture with a starting proportion of 25% bvg– genotype cells at the beginning of the fermentation. The diamond shaped points represent a culture with a starting proportion of 5% bvg– genotype cells at the beginning of the fermentation.
Figure 5:
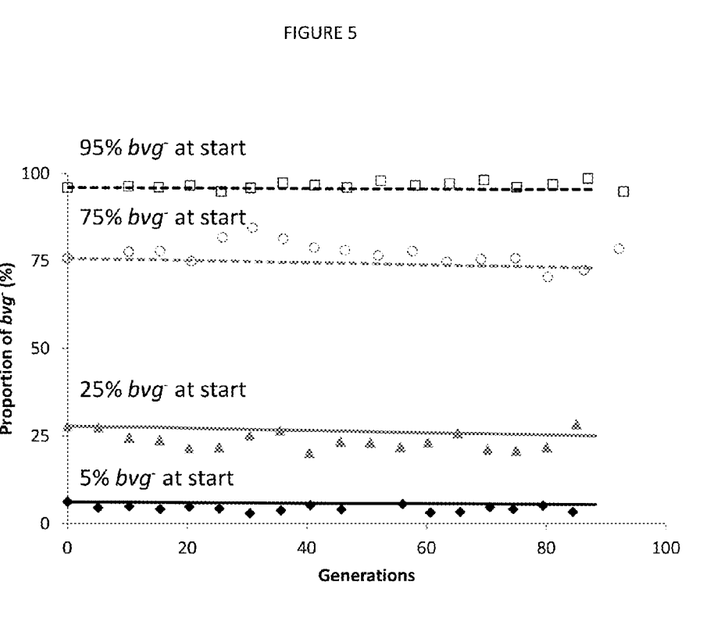
FIG. 5 Graph depicting the proportion of bvg– genotype cells in 4 cultures fermented in the presence of 0.6 g/L of niacin against number of generations. The square shaped points represent a culture with a starting proportion of 95% bvg– genotype cells at the beginning of the fermentation. The circle shaped points represent a culture with a starting proportion of 75% bvg– genotype cells at the beginning of the fermentation. The triangular shaped points represent a culture with a starting proportion of 25% bvg– genotype cells at the beginning of the fermentation. The diamond shaped points represent a culture with a starting proportion of 5% bvg– genotype cells at the beginning of the fermentation.

Two 20 L-fermentations of B. pertussis were performed in parallel. The pre-culture steps were performed as described in example 2. The same pre-culture train was used to inoculate two 20 L-fermentors. The 20 L-fermentations were performed as described in example 1, except that the maximum stirring speed was set at 550 rpm in the first fermentation (COQ238; oxygen-sufficient conditions) and 280 rpm in the second fermentation (COQ239; oxygen-limited conditions). Fermentations were stopped when the carbon sources were completely exhausted, as evidenced by an abrupt stop in oxygen consumption.

The dissolved oxygen profile for both fermentations is compared in FIG. 3 (absolute dissolved oxygen calculated from online measurements of temperature, head pressure, and relative dissolved oxygen, using Henry's law). The biomass and PT yields are shown in Table 7. The limited oxygen supply (COQ239) had a negative effect on both the final biomass and PT concentration. The growth rate of the culture was also negatively affected under oxygen-limited conditions.

TABLE 7

Main fermentation parameters for 20 L-fermentations of B. pertussis under oxygen-sufficient (COQ238) or oxygen-limited (COQ239) conditions.

|  | COQ238 | COQ239 |
|---|---|---|
| Oxygen supply | sufficient | limited |
| Total fermentation time* | 35 h | 44 h |
| Final biomass ($OD_{650\ nm}$) | 6.9 | 5.9 |
| PT concentration at end of fermentation | 22.1 mg/L | 13.9 mg/L |
| Specific PT production at end of fermentation | 3.2 mg $L^{-1}$ $OD_{650\ nm}^{-1}$ | 2.4 mg $L^{-1}$ $OD_{650\ nm}^{-1}$ |

*The total fermentation time is defined as the time at which oxygen consumption decreases (as a consequence of glutamate exhaustion), resulting in a decrease in stirring speed.

Example 7

Use of Yeast Extract to Inhibit PT Production

Two 20 L-fermentations of B. pertussis were performed in parallel. The pre-culture steps were performed as described in example 2, except for Na-L-Glutamate concentration (20 g/L). The 20 L-fermentations were performed as described in example 1, except for the following adaptations to the medium composition: in fermentation COQ199, yeast extract was added to the medium at a concentration of 20 g/L, whereas in fermentation COQ182, casein hydrolysate was added at a concentration of 10 g/L. In both fermentations, foaming was controlled by automatic addition of a polydimethylsiloxane emulsion via a foam controller. Fermentations were stopped when the carbon sources were completely exhausted, as evidenced by an abrupt stop in oxygen consumption.

The biomass and PT yields are shown in Table 8. The use of yeast extract (COQ199) rather than casein hydrolysate (COQ182) had a positive effect on biomass concentration, and a negative effect on PT production (43% decrease compared to reference conditions).

TABLE 8

Main fermentation parameters for 20 L-fermentations of B. pertussis in medium containing 20 g/L yeast extract (COQ199) or 10 g/L casein hydrolysate (COQ182).

|  | COQ182 | COQ199 |
|---|---|---|
| Complex raw material in medium | Casein hydrolysate 10 g/L | Yeast extract 20 g/L |
| Final biomass ($OD_{650\ nm}$) | 10.0 | 15.2 |
| PT concentration at end of fermentation | 34.4 mg/L | 19.5 mg/L |
| Specific PT production at end of fermentation | 3.4 mg $L^{-1}$ $OD_{650\ nm}^{-1}$ | 1.3 mg $L^{-1}$ $OD_{650\ nm}^{-1}$ |

Example 8

Use of High Proline Concentration and Low Sodium Concentration to Inhibit PT Production Three 20 L-fermentations of B. pertussis were performed in parallel. The pre-culture steps were performed as described in example 2, except for medium composition, which was as described in example 4. The 20 L-fermentations were performed as described in example 1, except for medium composition: in fermentation COQ280, proline was added to obtain a final concentration of 1 g/L, whereas in fermentation COQ278, the proline concentration was 12 g/L. In order to keep a similar amount of carbon source between the two conditions, the glutamate (provided as sodium glutamate) concentration was reduced from 20 g/L in fermentation COQ280 to 7 g/L in fermentation COQ278. In fermentation COQ281, the proline and glutamate concentration were identical to COQ278, but NaCl was added at a concentration of 4 g/L to compensate for the reduction in sodium glutamate compared to COQ280. Fermentations were stopped when the carbon sources were completely exhausted, as evidenced by an abrupt stop in oxygen consumption.

The biomass and PT yields are shown in Table 9. When proline was present at a high concentration (COQ278), a significant reduction in PT production was observed (58% decrease compared to COQ280). This effect was partially relieved when NaCl was added to compensate for the decreased sodium glutamate concentration (COQ281; 37% decrease compared to COQ280). These observations indicate that both high proline concentration and low sodium concentration have a negative effect on PT production, and that these effects are additive (i.e. non-redundant).

TABLE 9

Main fermentation parameters for 20 L-fermentations of B. pertussis in medium containing 1 g/L proline (COQ280), 12 g/L proline (COQ278), or 12 g/L proline and 4 g/L NaCl (COQ281).

|  | COQ280 | COQ278 | COQ281 |
|---|---|---|---|
| Proline concentration (g/L) | 1 | 12 | 12 |
| Sodium Glutamate concentration (g/L) | 20 | 7 | 7 |
| NaCl concentration (g/L) | 0 | 0 | 4 |
| Final biomass ($OD_{650nm}$) | 9.7 | 11.3 | 9.8 |
| PT concentration at end of fermentation | 19.0 mg/L | 8.0 mg/L | 12.0 mg/L |
| Specific PT production at end of fermentation | 2.0 mg $L^{-1}$ $OD_{650\ nm}^{-1}$ | 0.7 mg $L^{-1}$ $OD_{650\ nm}^{-1}$ | 1.2 mg $L^{-1}$ $OD_{650\ nm}^{-1}$ |

Example 9

Use of High Phosphate Concentration to Inhibit PT Production

Two 20 L-fermentations of B. pertussis were performed in parallel. The pre-culture steps were performed as described in example 8. The 20 L-fermentations were performed as described in example 1, except for the following adaptations to the medium composition: in fermentation COQ280, $KH_2PO_4$ was added at a concentration of 0.5 g/L, whereas in fermentation COQ279, the $KH_2PO_4$ concentration was 0.8 g/L. Fermentations were stopped when the carbon sources were completely exhausted, as evidenced by an abrupt stop in oxygen consumption.

The biomass and PT yields are shown in Table 10. When phosphate was present at a high concentration, a significant reduction in PT production was observed (32% decrease compared to COQ280).

TABLE 10

Main fermentation parameters for 20 L-fermentations of *B. pertussis* in medium containing 0.5 g/L (COQ280) or 0.8 g/L (COQ279) $KH_2PO_4$.

| | COQ280 | COQ279 |
|---|---|---|
| $KH_2PO_4$ concentration (g/L) | 0.5 | 0.8 |
| Final biomass ($OD_{650\ nm}$) | 9.7 | 9.2 |
| PT concentration at end of fermentation | 19 mg/L | 13 mg/L |
| Specific PT production at end of fermentation | 2.0 mg $L^{-1}$ $OD_{650\ nm}^{-1}$ | 1.4 mg $L^{-1}$ $OD_{650\ nm}^{-1}$ |

Example 10

Combination of High Phosphate Concentration, High Proline Concentration, and Low Sodium Concentration to Inhibit PT Production Two 20 L-fermentations of *B. pertussis* were performed in parallel. The pre-culture steps were performed as described in example 8. The 20 L-fermentations were performed as described in example 1, except for the following adaptations to the medium composition (detailed in Table 11): in fermentation COQ269, the medium contained a combination of high phosphate ($KH_2PO_4$ 0.8 g/L), low sodium (sodium glutamate 7 g/L and no NaCl), and high proline (12 g/L) concentration. Fermentations were stopped when the carbon sources were completely exhausted, as evidenced by an abrupt stop in oxygen consumption.

The biomass and PT yields are shown in Table 11. In the presence of high phosphate, low sodium, and high proline concentrations (COQ269), no negative impact on the biomass yield was observed. However, PT production was severely reduced (84% decrease compared to COQ280).

TABLE 11

Main fermentation parameters for 20 L-fermentations of *B. pertussis* in medium containing a combination of high phosphate, low sodium, and high proline concentration.

| | COQ280 | COQ269 |
|---|---|---|
| Proline concentration (g/L) | 1 | 12 |
| Sodium Glutamate concentration (g/L) | 20 | 7 |
| NaCl concentration (g/L) | 0 | 0 |
| $KH_2PO_4$ concentration (g/L) | 0.5 | 0.8 |
| Final biomass ($OD_{650\ nm}$) | 9.7 | 11.5 |
| PT concentration at end of fermentation | 19 mg/L | 3 mg/L |
| Specific PT production at end of fermentation | 2.0 mg $L^{-1}$ $OD_{650\ nm}^{-1}$ | 0.3 mg $L^{-1}$ $OD_{650\ nm}^{-1}$ |

Example 11

Use of High Cysteine Concentration to Inhibit PT Production

Two 20 L-fermentations of *B. pertussis* were performed in parallel. The pre-culture steps were performed as described in example 2. The 20 L-fermentations were performed as described in example 1, except for the following adaptations of the medium composition: in fermentation COQ280, L-cysteine was added at a concentration of 0.04 g/L, whereas in fermentation COQ396, the L-cysteine concentration was 0.2 g/L. Fermentations were stopped when the carbon sources were completely exhausted (when there is an abrupt stop in oxygen consumption).

The biomass and PT yields are shown in Table 12. When L-cysteine was present at a high concentration, a significant reduction in PT production was observed (32% decrease compared to COQ280).

TABLE 12

Main fermentation parameters for 20 L-fermentations of *B. pertussis* in medium containing 0.04 g/L (COQ280) or 0.2 g/L (COQ396) L-cysteine.

| | COQ280 | COQ396 |
|---|---|---|
| L-cysteine concentration (g/L) | 0.04 | 0.2 |
| Final biomass ($OD_{650\ nm}$) | 9.7 | 11.0 |
| PT concentration at end of fermentation | 19 mg/L | 13 mg/L |
| Specific PT production at end of fermentation | 2.0 mg $L^{-1}$ $OD_{650\ nm}^{-1}$ | 1.2 mg $L^{-1}$ $OD_{650\ nm}^{-1}$ |

Example 12

Long-Term Control of $bvg^-$ Take-Over with Niacin

Examples 3 and 4 indicate that niacin at 0.6 g/L can be used to control the take-over of $bvg^-$ cells over a limited number of generations, even starting from a relatively low proportion of bvg− cells (up to 6%). In order to extend this observation to a higher number of generations and a wider range of initial proportion of $bvg^-$ cells, two groups of four serial shake-flask cultures were performed, as described below.

First, one $bvg^+$ isolate and one $bvg^-$ isolate were inoculated separately in 100 ml fresh medium adapted from Stainer and Scholte (as described in example 4) (J. Gen. Microbiol. 63:211-220 (1971)), and containing 0.004 g/L niacin. The two shake flasks were incubated for 24 h (+/−1 h) at 35° C. (+/−1° C.) and 150 rpm. Cells were harvested by centrifugation, washed twice with fresh medium, and resuspended in fresh medium. Different mixes of the two cell suspensions were then prepared, in order to obtain suspensions containing 93.8%, 72.1%, 4.2%, or 4% $bvg^-$ cells. Each of these four mixed cell suspensions was used to inoculate two separate shake flasks containing 100 ml fresh medium with either 0.004 g/L niacin or 0.6 g/L niacin. After incubation for 24 h (+/−1 h) at 35° C. (+/−1° C.) and 150 rpm, each culture was used to inoculate a shake flask containing 100 ml of fresh medium containing the same niacin concentration. For each of the 8 shake flask cultures, the procedure was repeated 17 times in total, in order to reach a total number of generations of approximately 90 to 100. At the end of each passage (approximately 5 generations), the proportion of $bvg^+$ and $bvg^-$ cells was measured by plating appropriate dilutions of the culture on BG medium. Results are depicted in FIG. 4 for the four serial cultures with niacin 0.004 g/L, and in FIG. 5 for the four serial cultures with niacin 0.6 g/L.

These results demonstrate that the use of niacin at 0.6 g/L rather than 0.004 g/L, can effectively control the take-over of $bvg^-$ cells, independently of the initial proportion of these cells. They also show that this control is effective for up to 100 generations, which typically corresponds to the number of generations required to produce a working cell bank and sufficient biomass (pre-culture train) for the inoculation of an industrial-scale fermentation, starting from a newly isolated *B. pertussis* strain.

We claim:

1. A fermentation process for culturing a species of *Bordetella*, comprising the following steps:
   a) providing a sample of bacterial cells of a *Bordetella* species in a first culture medium comprising at least one *Bordetella* virulence gene (bvg) modulator, wherein the bvg modulator is niacin at a concentration of greater than or equal to 0.2 g/L and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

2. The fermentation process of claim 1 wherein the *Bordetella* species is a species selected from the group consisting of *Bordetella pertussis*, *Bordetella parapertussis*, and *Bordetella bronchiseptica*.

3. The fermentation process of claim 1 wherein step b) comprises less than 40 generations of growth.

4. A fermentation process for culturing a species of *Bordetella*, comprising the following steps:
   a) providing a sample of bacterial cells of a *Bordetella* species in a first culture medium comprising at least one *Bordetella* virulence gene (lava) modulator, wherein the bvg modulator is a sulphate salt at a concentration of between 0.04 mM and 40 mM, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

5. A fermentation process for culturing a species of *Bordetella*, comprising the following steps:
   a) providing a sample of bacterial cells of a *Bordetella* species in a first culture medium comprising at least one *Bordetella* virulence gene (lava) modulator, wherein the bvg modulator is a phosphate salt at a concentration of between 0.4 g/L and 20 g/L, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

6. A fermentation process for culturing a species of *Bordetella*, comprising the following steps:
   a) providing a sample of bacterial cells of a *Bordetella* species in a first culture medium comprising at least one *Bordetella* virulence gene (bvg) modulator, wherein the bvg modulator is sucrose at a concentration of between 10 mM and 100 mM, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

7. A fermentation process for culturing a species of *Bordetella*, comprising the following steps:
   a) providing a sample of bacterial cells of a *Bordetella* species in a first culture medium comprising at least one *Bordetella* virulence gene (bvg) modulator, wherein the bvg modulator is selected from the group consisting of yeast extract, tryptic soy agar, tryptose phosphate, infusions of brain and heart tissue, and peptones, and wherein the concentration of the bvg modulator is between 1 g/L and 40 g/L, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

8. A fermentation process for culturing a species of *Bordetella*, comprising the following steps:
   a) providing a sample of bacterial cells of a *Bordetella* species in a first culture medium comprising at least one *Bordetella* virulence gene (bvg) modulator, wherein the bvg modulator is proline at a concentration of between 0.25 g/L and 50 g/L, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

9. A fermentation process for culturing a species of *Bordetella*, comprising the following steps:
   a) providing a sample of bacterial cells of a *Bordetella* species in a first culture medium comprising at least one *Bordetella* virulence gene (bvg) modulator, wherein the bvg modulator comprises sodium ions at a concentration between 100 mM and 2000 mM, and wherein the sample predominantly comprises *Bordetella* cells having a bvg+ genotype;
   b) incubating the sample in the first culture medium comprising the at least one bvg modulator for at least five generations of growth, thereby producing a mature culture; and
   c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

10. A fermentation process for culturing a species of *Bordetella*, comprising the following steps:
    a) providing a sample of bacterial cells of a *Bordetella* species in a first culture medium comprising at least one *Bordetella* virulence gene (bvg) modulator, wherein the bvg modulator is glutathione at a concentration of between 0.15 g/L and 20 g/L, and wherein the sample predominantly comprises *Bordetella* cells having a bvg+ genotype;
    b) incubating the sample in the first culture medium comprising the at least one bvg modulator for at least five generations of growth, thereby producing a mature culture; and
    c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

11. The fermentation process of claim 1 wherein between 2% and 10% of the mature culture is bvg− genotype at the beginning of step c).

12. The fermentation process of claim 1 wherein at least part of step b) is carried out in a vessel greater than or equal to 25 ml in volume.

13. The fermentation process of claim 12 wherein the vessel is a fermentor with a working volume of: between 5 and 10000 liters.

14. The fermentation process of claim 1 wherein step c) is carried out at a temperature between 32° C. and 45° C.

15. The fermentation process of claim 1 wherein a mechanical foam breaker is used in step c).

16. The fermentation process of claim 1 wherein step b) comprises a pre-culture phase.

17. The fermentation process of claim 1 further comprising a cell banking phase between step a) and step b).

18. The fermentation process of claim 1 wherein more than 85% of the sample of the bacteria is Bvg+ genotype.

19. The fermentation process of claim 1 wherein step b) comprises at least 8 generations of growth.

20. The fermentation process of claim 1 wherein step b) is carried out at a temperature of between 20° C. and 45° C.

21. The fermentation process of claim 1 wherein step b) is carried out at a pH between 6.5 and 7.8.

22. The fermentation process of claim 1 wherein step c) is carried out at a pH between 6.5 and 7.8.

23. The fermentation process of claim 1 wherein step b) is carried out in the presence of between 10% and 50% dissolved oxygen.

24. The fermentation process of claim 1 wherein step c) is carried out in the presence of between 0% and 50% dissolved oxygen.

25. The fermentation process of claim 1 further comprising a step d) of purifying the virulence factor to produce a purified virulence factor.

26. The fermentation process of claim 1 wherein the bvg modulator is niacin at a concentration of greater than or equal to 0.3 g/l.

27. The fermentation process of claim 1 wherein the bvg modulator is niacin at a concentration of at least 0.6 g/L.

28. A fermentation process for culturing a species of *Bordetella*, comprising the following steps:
    a) providing a sample of bacterial cells of a *Bordetella* species in a first culture medium comprising at least one *Bordetella* virulence gene (bvg) modulator, wherein the bvg modulator is cysteine at a concentration of between 0.8 mM and 250 mM, and wherein the sample predominantly comprises *Bordetella* cells having a bvg+ genotype;
    b) incubating the sample in the first culture medium comprising the at least one bvg modulator for at least five generations of growth, thereby producing a mature culture; and
    c) incubating the mature culture in a second culture medium in the absence of the at least one bvg modulator for at least five generations of growth; wherein step c) occurs after step b), and wherein in step (c) at least one virulence factor selected from the group consisting of *Pertussis* Toxin (PT), Filamentous Haemagglutinin (FHA), Pertactin (PRN) and fimbrial agglutinogen is expressed.

29. The fermentation process of claim claim 28 wherein the bvg modulator is cysteine at a concentration of at least 1.65 mM.

30. The fermentation process of claim 28 wherein the *Bordetella* species is a species selected from the group consisting of *Bordetella pertussis, Bordetella parapertussis*, and *Bordetella bronchiseptica*.

31. The fermentation process of claim 28 wherein step b) comprises less than 40 generations of growth.

32. The fermentation process of claim 28 wherein between 2% and 10% of the mature culture is bvg− genotype at the beginning of step c).

33. The fermentation process of claim 28 wherein at least part of step b) is carried out in a fermentor with a working volume of: between 5 and 10000 liters.

34. The process of claim 28 wherein step c) is carried out at a temperature between 32° C. and 45° C.

35. The fermentation process of claim 28 wherein a mechanical foam breaker is used in step c).

36. The fermentation process of claim 28 wherein step b) comprises a pre-culture phase.

37. The fermentation process of claim 28 further comprising a cell banking phase between step a) and step b).

38. The fermentation process of claim 28 wherein more than 85% of the sample of the bacteria is Bvg+ genotype.

39. The fermentation process of claim 28 wherein step b) comprises at least 8 generations of growth.

40. The fermentation process of claim 28 wherein step b) is carried out at a temperature of between 20° C. and 45° C.

41. The fermentation process of claim 28 wherein step b) is carried out at a pH between 6.5 and 7.8.

42. The fermentation process of claim 28 wherein step c) is carried out at a pH between 6.5 and 7.8.

43. The fermentation process of claim 28 wherein step b) is carried out in the presence of between 10% and 50% dissolved oxygen.

44. The fermentation process of claim 28 wherein step c) is carried out in the presence of between 0% and 50% dissolved oxygen.

45. The fermentation process of claim 28 further comprising a step d) of purifying the virulence factor to produce a purified virulence factor.

* * * * *